United States Patent [19]

Bays et al.

[11] Patent Number: 4,997,831
[45] Date of Patent: Mar. 5, 1991

[54] LACTAM DERIVATIVES

[75] Inventors: David E. Bays, Ware; Ian H. Coates, Hertford; Alexander W. Oxford; Peter C. North, both of Royston, all of England

[73] Assignee: Glaxo Group Limited, England

[21] Appl. No.: 401,249

[22] Filed: Aug. 31, 1989

[30] Foreign Application Priority Data

Sep. 1, 1988 [GB] United Kingdom ............... 8820649
Feb. 8, 1989 [GB] United Kingdom ............... 8902757

[51] Int. Cl.$^5$ ................... C07D 471/04; A61K 31/475
[52] U.S. Cl. ..................................... 514/211; 514/215; 514/219; 514/228.2; 514/229.5; 514/287; 540/546; 540/555; 544/14; 544/99; 544/343; 546/70
[58] Field of Search ............................ 544/14, 99, 343; 546/70; 540/546, 555; 514/211, 215, 219, 228.2, 229.5, 287

[56] References Cited

U.S. PATENT DOCUMENTS

| | | | |
|---|---|---|---|
| 3,299,078 | 1/1967 | Prachter | 546/67 |
| 3,914,421 | 10/1975 | Rajagopalan | 544/99 |
| 4,013,652 | 3/1977 | Rajagopalan | 544/99 |
| 4,115,577 | 9/1978 | Rajagopalan | 544/14 |
| 4,183,936 | 1/1980 | Rajagopalan | 544/14 |
| 4,939,136 | 7/1990 | Haeck et al. | 514/183 |

FOREIGN PATENT DOCUMENTS

| | | |
|---|---|---|
| 297651 | 1/1989 | European Pat. Off. . |
| 306323 | 3/1989 | European Pat. Off. . |
| 322016 | 6/1989 | European Pat. Off. . |
| 327307 | 8/1989 | European Pat. Off. . |
| 0377238 | 7/1990 | European Pat. Off. . |
| 3740352 | 6/1988 | Fed. Rep. of Germany . |

Primary Examiner—Mary C. Lee
Assistant Examiner—Jacqueline Haley
Attorney, Agent, or Firm—Bacon & Thomas

[57] ABSTRACT

The invention provides lactam derivatives of the general formula (I)

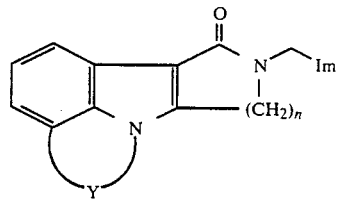

wherein n represents 2 or 3; Im represents an imidazolyl group of the formula:

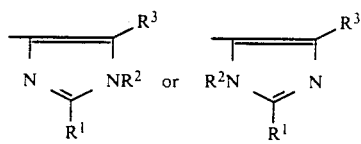

wherein one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same or different, represents a hydrogen atom or a $C_{1-6}$alkyl group; Y represents a group $-(CH_2)_m-$, wherein m represents 2, 3 or 4; or Y represents a group $-X(CH_2)_p-$, wherein p represents 2 or 3, X represents an oxygen or a sulphur atom or a group $NR^4$, where $R^4$ is a $C_{1-6}$alkyl group, and X is attached to the benzene ring moiety of the molecule; and physiologically acceptable salts and solvates thereof.

The compounds of formula (I) are potent and selective antagonists of 5-hydroxytryptamine at 5-HT$_3$ receptors and are useful, for example in the treatment of psychotic disorders, anxiety and nausea and vomiting.

7 Claims, No Drawings

LACTAM DERIVATIVES

This invention relates to lactam derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at 5-HT$_3$ receptors have been described previously.

Thus for example German Offenlegungsschrift No. 3740352 discloses compounds which may be represented by the general formula:

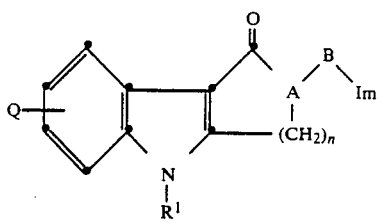

wherein Im represents an imidazolyl group of the formula:

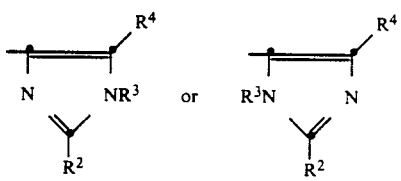

R$^1$ represents a hydrogen atom or a group selected from C$_{1-6}$alkyl, C$_{3-6}$alkenyl, C$_{3-10}$alkynyl, C$_{3-7}$cycloalkyl, C$_{3-7}$cycloalkylC$_{1-4}$alkyl-, phenyl, phenylC$_{1-3}$alkyl-, —CO$_2$R$^5$, —COR$^5$, —CONR$^5$R$^6$ or —SO$_2$R$^5$ (wherein R$^5$ and R$^6$, which may be the same or different, each represents a hydrogen atom, a C$_{1-6}$alkyl or C$_{3-7}$cycloalkyl group, or a phenyl or phenylC$_{1-4}$alkyl-group, in which the phenyl group is optionally substituted by one or more C$_{1-4}$alkyl, C$_{1-4}$alkoxy or hydroxy groups or halogen atoms, with the proviso that R$^5$ does not represent a hydrogen atom when R$^1$ represents a group —CO$_2$R$^5$ or —SO$_2$R$^5$); one of the groups represented by R$^2$, R$^3$ and R$^4$ is a hydrogen atom or a C$_{1-6}$alkyl, C$_{3-7}$cycloalkyl, C$_{3-6}$alkenyl, phenyl or phenylC$_{1-3}$alkyl-group, and each of the other two groups, which may be the same or different, represents a hydrogen atom or a C$_{1-6}$alkyl group; Q represents a hydrogen or a halogen atom, or a hydroxy, C$_{1-4}$alkoxy, phenylC$_{1-3}$alkoxy- or C$_{1-6}$alkyl group or a group —NR$^7$R$^8$ or —CONR$^7$R$^8$ (wherein R$^7$ and R$^8$, which may be the same or different, each represents a hydrogen atom or a C$_{1-4}$alkyl or C$_{3-4}$alkenyl group, or together with the nitrogen atom to which they are attached form a saturated 5 to 7 membered ring); n represents 1, 2 or 3; and A—B represents the group CH—CH$_2$ or C=CH; and physiologically acceptable salts and solvates thereof.

We have now found a novel group of compounds which differ in structure from those described previously, and which are potent antagonists of the effect of 5-HT at 5-HT$_3$ receptors.

The present invention provides a tetracyclic lactam of the general formula (I):

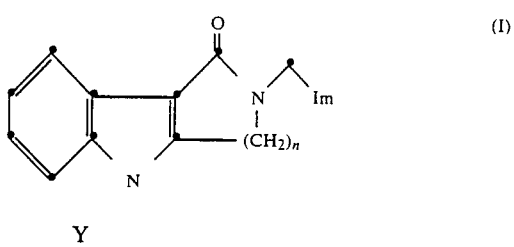

wherein n represents 2 or 3; Im represents an imidazolyl group of the formula:

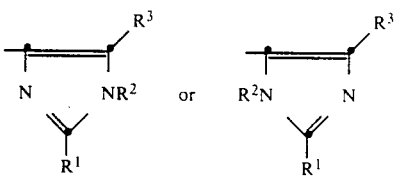

wherein one of the groups represented by R$^1$, R$^2$ and R$^3$ is a hydrogen atom or a C$_{1-6}$alkyl, C$_{3-7}$cycloalkyl, C$_{3-6}$alkenyl, phenyl or phenylC$_{1-3}$alkyl- group, and each of the other two groups, which may be the same or different, represents a hydrogen atom or a C$_{1-6}$alkyl group; Y represents a group —(CH$_2$)$_m$—, wherein m represents 2, 3 or 4; or Y represents a group —X(CH$_2$)$_p$—, wherein p represents 2 or 3, X represents an oxygen or a sulphur atom or a group NR$^4$, where R$^4$ is a C$_{1-6}$alkyl group, and X is attached to the benzene ring moiety of the molecule; and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl or aryl sulphonates (e.g. methanesulphonates or p-toluenesulphonates), phosphates, citrates, succinates, tartrates, acetates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, propyl, prop-2-yl, butyl, but-2-yl, 2-methylprop-2-yl, pentyl, pent-3-yl or hexyl. A C$_{3-6}$alkenyl group may be, for example, a propenyl or butenyl group. When R$^2$ represents a C$_{3-6}$alkenyl group, the double bond may not be adjacent to the nitrogen atom. A phenylC$_{1-3}$alkyl- group may be, for example, a benzyl, phenethyl or 3-phenylpropyl group. A C$_{3-7}$cycloalkyl group may be, for example, a cyclopropyl, cyclobutyl, cyclopentyl, cyclohexyl or cycloheptyl group.

A preferred class of compounds of formula (I) is that in which $R^1$, $R^2$ and $R^3$ each independently represent a hydrogen atom or a $C_{1-4}$alkyl (e.g. methyl) group. A further preferred class of compounds is that wherein $R^1$ and $R^2$ each represent a hydrogen atom, and $R^3$ is a $C_{1-3}$alkyl (e.g. methyl) group.

Another preferred class of compounds of formula (I) is that in which Y represents the group —(CH$_2$)$_2$—, —(CH$_2$)$_3$— or —O(CH$_2$)$_2$—, more preferably —(CH$_2$)$_2$— or —(CH$_2$)$_3$—.

Preferred compounds according to the invention are: 5,6,9,10-tetrahydro-10-[(5-methyl-1H-imidazol-4-yl)methyl]-4H-pyrido[3',4':4,5]pyrrolo[3,2,1-ij]quinolin-11(8H)-one; 4,5,7,8-tetrahydro-9-[(5-methyl-1H-imidazol-4-yl)methyl]pyrido[4,3-b]pyrrolo[3,2,1-hi]indol-10(9H)-one; 4,5,7,8,9,10-hexahydro-10-[(5-methyl-1H-imidazol-4-yl)methyl]-11H-azepino[4,3-b]pyrrolo[3,2,1-hi]indol-11-one; and their physiologically acceptable salts and solvates.

The potent and selective antagonism of 5-HT at 5-HT$_3$ receptors by the compounds of the invention may be demonstrated by their ability to inhibit 3-(5-methyl-1H-imidazol-4-yl)-1-[1-(methyl-t$_3$)-1H-indol-3-yl]-1-propanone binding in rat entorhinal cortex homogenates (following the general procedure described by G. Kilpatrick et al. in Nature, 1987, 330, 746), and/or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; obesity and conditions such as bulimia; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; obesity and conditions such as bulimia; pain; dependency on drugs or substances of abuse; depression; or dementia or another cognitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, cimetidine, famotidine, nizatidine or roxatidine) or $H^+K^+ATPase$ inhibitors (e.g. omeprazole). In the treatment of nausea and vomiting, compounds of formula (I) may also be administered in combination with dexamethasone or a cyclo-oxygenase inhibitor such as piroxicam.

A proposed dose of the compounds of the invention for administration to man (of approximately 70 kg body weight) is 0.001 to 100 mg, preferably 0.01 to 50 mg, of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$ to $R^3$, n, Y and Im are as defined for compounds of general formula (I) unless otherwise stated.

According to a first general process (A) a compound of general formula (I) may be prepared by alkylating a compound of formula (II):

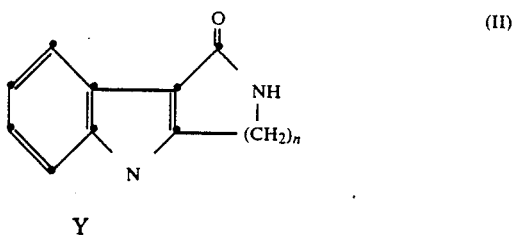

with a compound of formula (III):

or a protected derivative thereof, wherein L represents a leaving atom or group, such as a halogen atom (e.g. chlorine, bromine or iodine), or an acyloxy group (e.g. trifluoroacetyloxy or acetoxy), or a sulphonyloxy group (e.g. trifluoromethanesulphonyloxy, p-toluenesulphonyloxy or methanesulphonyloxy); followed where necessary by removal of any protecting groups. L is preferably a halogen atom (e.g. a chlorine atom).

The reaction may be carried out in an inert solvent such as an ether (e.g. dimethoxyethane, diglyme or tetrahydrofuran), a substituted amide (e.g. dimethyl-formamide or N-methylpyrrolidone), an aromatic hydrocarbon (e.g. toluene), a ketone (e.g. acetone), or dimethyl sulphoxide, at a temperature between ambient and 100° C., in the presence of a base. Suitable bases include alkali metal hydrides (e.g. sodium hydride), alkali metal carbonates (e.g. sodium carbonate), alkali metal amides (e.g. sodium amide), alkali metal alkoxides (e.g. potassium t-butoxide) or alkali metal hydroxides (e.g. sodium or potassium hydroxide).

According to another general process (B), a compound of general formula (I) may be converted into another compound of formula (I) using conventional techniques. Such conventional techniques include hydrogenation and alkylation using protection and deprotection where necessary.

Thus, according to one embodiment of the interconversion process (B), hydrogenation may be used to convert an alkenyl substituent into an alkyl substituent. Hydrogenation according to general process (B) may be effected using conventional procedures, for examples, using hydrogen in the presence of a catalyst, as described in published European Patent specification No. 242973.

The term 'alkylation' according to general process (B) includes the introduction of groups such as cycloalkyl, alkenyl or phenalkyl groups.

Thus, for example, a compound of formula (I) in which $R^2$ represents a $C_{1-6}$alkyl, $C_{3-7}$cycloalkyl, $C_{3-6}$alkenyl or phenyl$C_{1-3}$alkyl- group may be prepared by alkylating the corresponding compound of formula (I) in which $R^2$ represents a hydrogen atom, using conventional procedures, for example as described in published European Patent specification No. 242973. Thus the reactions may be effected using an appropriate alkylating agent of formula $R^5Z$ (where $R^5$ is the group to be introduced and Z is a leaving atom or group), preferably in the presence of a base.

It should be appreciated that in the above transformations it may be necessary or desirable to protect any sensitive groups in the molecule of the compound in question to avoid undesirable side reactions. For example, it may be necessary to protect the imidazole nitrogen atom, for example with an arylmethyl (e.g. trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example, a trityl group may be cleaved by acid hydrolysis (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may be removed by alkaline hydrolysis.

Compounds of formula (II) may be prepared, for example, by cyclising a compound of formula (IV):

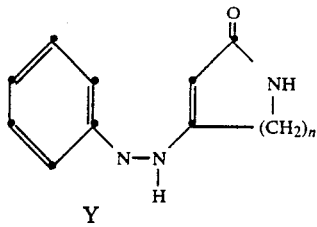

(IV)

or a salt thereof. The cyclisation may be carried out in aqueous or non-aqueous media, optionally in the presence of an acid catalyst. When an acid catalyst is used, this may be, for example, an inorganic acid such as concentrated sulphuric or hydrochloric acid. The acid catalyst may also act as the reaction solvent. In an anhydrous reaction medium, the acid catalyst may alternatively be a Lewis acid such as zinc chloride. The cyclisation reaction may conveniently be carried out at a temperature in the range of 20° to 200° C. When no acid catalyst is used, the cyclisation may be effected thermally, by heating in a high boiling organic solvent, such as diethylene glycol, conveniently at a temperature in the range 100° to 200° C.

Compounds of formula (IV) may be prepared, for example, by the reaction of a compound of formula (V):

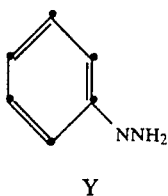

(V)

or a salt thereof, with a compound of formula (VI):

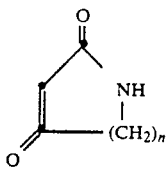

(VI)

or a protected derivative thereof, in a suitable solvent such as an alcohol (e.g. ethanol), and at a temperature of, for example, from 20° to 100° C.

Alternatively, compounds of formula (II) may be prepared directly by the reaction of a compound of formula (V), or a salt thereof, with a compound of formula (VI), or a protected derivative thereof, using the appropriate conditions as described above. Compounds of formula (IV) may be isolated as intermediates in the above reaction.

Compounds of formula (III) and protected derivatives thereof, are either known, or may be prepared, for example, by the methods described in German Offenlegungsschrift No. 3740352.

Compounds of formulae (V) and (VI) are either known, or may be prepared from known compounds by conventional procedures.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in °C. Thin layer chromatography (t.l.c.) was carried out on silica, and flash column chromatography (FCC) was carried out on silica (Merck 9385). Solvent System A as used for chromatography denotes dichloromethane:ethanol: 0.88 ammonia solution. Organic extracts were dried, where indicated, over magnesium sulphate.

INTERMEDIATE 1

5,6,9,10-Tetrahydro-4H-pyrido[3',4':4,5]pyrrolo[3,2,1-ij]quinolin-11(8H)-one

A solution of 2-amino-1,2,3,4-tetrahydroquinoline hemisulphate (500 mg) and 2,4-dioxopiperidine (287 mg) in absolute ethanol (20 ml) was kept under nitrogen for 20 h. The solvent was removed in vacuo to leave a gum (700 mg) which was treated with concentrated sulphuric acid (7 ml) for 15 min. The resulting solution was neutralised with 8% sodium bicarbonate solution (200 ml) and extracted with dichloromethane (3×100 ml). The combined, dried organic extracts were evaporated to give a solid (470 mg) which was purified by FCC eluting with System A (400:10:1) to give the title compound (230 mg) as a solid, m.p. 254°–256°.

INTERMEDIATE 2

4,5,7,8-Tetrahydropyrido[4,3-b]pyrrolo[3,2,1-hi]indol-10(9H)-one

A solution of 1-amino-indoline hydrochloride (1.0 g) and 2,4-dioxopiperidine (663 mg) in absolute ethanol (40 ml) was stirred under nitrogen for 48 h. The solvent was removed in vacuo and the residue was dissolved in diethylene glycol (30 ml) and heated at 200° for 2 h. The solution was allowed to cool, poured into water (200 ml) and extracted with dichloromethane (3×100 ml). The combined, dried organic extracts were evaporated to give an oil (ca. 2.5 g) which was purified by short path column chromatography on silica gel (Merck 7729) eluting with System A (400:10:1) to give the title compound (330 mg) as a solid, m.p. 265°–267°.

INTERMEDIATE 3

3,4-Dihydro-2H-1,4-benzoxazin-4-amine

A cold (0°) solution of sodium nitrite (2.6 g) in water (12.5 ml) was added dropwise to a cold (0°) stirred solution of 3,4-dihydro-2H-1,4-benzoxazine (4.9 g) in water (27.5 ml) and concentrated hydrochloric acid (9.5 ml). The mixture was stirred at 0°–5° for 1.5 h, then extracted with ether (3×60 ml). The combined, dried organic extracts were evaporated to give a solid which was dissolved in a mixture of acetic acid (11 ml), water (11 ml) and ethanol (17 ml) and added dropwise to a vigorously stirred suspension of zinc powder (25 g) in ethanol (32 ml) at 40°–50°. After 30 min the mixture was cooled and filtered, and the filtrate was evaporated to dryness. The residue was treated with 5N sodium hydroxide solution (300 ml) and extracted with ether (3×100 ml). The combined, dried organic extracts were evaporated to give an oil (ca. 5.3 g) which was purified by FCC eluting with hexane:ethyl acetate (4:1) to give the title compound (3.2 g) as an oil, t.l.c. (hexane:ethyl acetate, 4:1) Rf 0.25.

INTERMEDIATE 4

1,2,9,10-Tetrahydropyrido[3',4':4,5]pyrrolo[1,2,3-de][1,4]benzoxazin-7(8H)-one A solution of 4-amino-3,4-dihydro-2H-1,4-benzoxazine (1.0 g) and 2,4-dioxopiperidine (753 mg) in absolute ethanol (40 ml) was stirred under nitrogen for 1.5 h. The solvent was removed in vacuo and the residue was dissolved in diethylene glycol (30 ml) and heated at 100° for 1 h, then at 150° for 2 h. The solution was allowed to cool, poured into water (200 ml) and extracted with dichloromethane (3×100 ml). The combined, dried organic extracts were evaporated to give a semi-solid (ca. 3 g) which was purified by FCC eluting with System A (400:10:1) to give the title compound (740 mg) as a solid, m.p. 298°–300°.

INTERMEDIATE 5

3-(2,3-Dihydro-1H-indol-1-yl)-2-cyclohexen-1-one

A mixture of indoline (5.39 g) and cyclohexane-1,3-dione (5.07 g) was heated at ca. 150° for 7 h. After cooling, the mixture was purified by FCC eluting with ethyl acetate: methanol (10:1) to give a solid (7.30 g) which was recrystallised from ethyl acetate: ether (ca. 4:1) to give the title compound (5.08 g), m.p. 85°–86°.

INTERMEDIATE 6

4,5,8,9-Tetrahydropyrrolo[3,2,1-jk]carbazol-10(7H)-one

A mixture of 3-(2,3-dihydro-1H-indol-1-yl)-2-cyclohexen-1-one (2.515 g), cupric acetate (4.71 g) and palladium (II) acetate (0.20 g) in dry dimethylformamide (40 ml) was heated at 135° under nitrogen for 4 h. The solvent was then removed under reduced pressure and the residue was suspended in methanol and then filtered. The filtrate was evaporated under reduced pressure and the resultant residue was purified by FCC eluting with ethyl acetate to give the title compound (0.36 g) as a solid. A sample (20 mg) was recrystallised from ethyl acetate to give the title compound (15 mg), m.p. 208°–210°.

INTERMEDIATE 7

4,5,8,9-Tetrahydropyrrolo[3,2,1-jk]carbazol-10(7H)-one oxime

A mixture of 4,5,8,9-tetrahydropyrrolo[3,2,1-jk]carbazol-10(7H)-one (364 mg) and hydroxylamine hydrochloride (479 mg) in pyridine (50 ml) was heated to 50° for 60 h, and was then poured into 2N hydrochloric acid (100 ml). The resultant precipitate was filtered off, washed with water (50 ml), and dried in vacuo at 50° for 6 h to give the title compound (140 mg). Filtration of the precipitate that formed subsequently in the filtrate gave a further crop of the title compound (104 mg), m.p. 271°–272°.

INTERMEDIATE 8

4,5,7,8,9,10-Hexahydro-11H-azepino[4,3-b]pyrrolo[3,2,1-hi]indol-11-one 4,5,8,9-Tetrahydropyrrolo[3,2,1-jk]carbazol-10(7H)-one oxime (244 mg) was added to polyphosphoric acid (20 ml) at 120°, and the mixture was stirred at 120° for 1 h. After cooling, the mixture was poured into water (150 ml) and extracted with dichloromethane: ethanol (10:1; 4×100 ml). The combined, dried organic extracts were evaporated under reduced pressure to give a solid (150 mg) which was purified by FCC eluting with System A (100:10:1) to give the title compound (92 mg), t.l.c. (System A, 100:10:1) Rf 0.47.

EXAMPLE 1

5,6,9,10-Tetrahydro-10-[(5-methyl-1H-imidazol-4-yl)methyl]-4H-pyrido[3',4':4,5]pyrrolo[3,2,1-ij]quinolin-11(8H)-one maleate Sodium hydride (60% dispersion in oil; 57 mg) was added to a stirred suspension of 5,6,9,10-tetrahydro-4H-pyrido[3',4':4,5]pyrrolo[3,2,1-ij]quinolin-11(8H)-one (270 mg) in dimethoxyethane (15 ml) and the mixture was heated at 50° for 6 h. The mixture was then treated with 4-(chloromethyl)-5-methyl-1-(triphenylmethyl)-1H-imidazole (522 mg) and stirring was continued at 50° for 18 h. Water (3 ml) and acetic acid (3 ml) were added and the solution was heated at reflux for 3 h. The mixture was poured into 8% sodium bicarbonate solution (60 ml) and extracted with dichloromethane (3×30 ml). The combined, dried organic extracts were evaporated to give a solid (810 mg) which was purified by FCC eluting with System A (200:10:1) to give a solid (324 mg). This material was dissolved in dichloromethane/absolute ethanol (3 ml) and treated with a solution of maleic acid (117 mg) in absolute ethanol (1 ml). The solvent was removed in vacuo and the residue was triturated with dry ether (3×5 ml) to give the title compound (415 mg), m.p. 146°–148°.

Water Analysis Found 0.56% w/w≡0.13 mol $H_2O$.
Analysis Found: C,62.8; H,5.5; N,12.55; $C_{19}H_{20}N_4O \cdot C_4H_4O_4 \cdot 0.13H_2O$ requires C,62.9; H,5.5; N,12.8%.

EXAMPLE 2

4,5,7,8-Tetrahydro-9-[(5-methyl-1H-imidazol-4-yl)methyl]pyrido[4,3-b]pyrrolo[3,2,1-hi]indol-10(9H)-one maleate Sodium hydride (60% dispersion in oil; 68 mg) was added to a stirred solution of 4,5,7,8-tetrahydropyrido[4,3-b]pyrrolo[3,2,1-hi]indol-10(9H)-one (300 mg) in dry dimethoxyethane (15 ml) under nitrogen, and the mixture was heated at 60° for 6 h. The mixture was then treated with 4-(chloromethyl)-5-methyl-1-(triphenylmethyl)-1H-imidazole (634 mg) and stirring was continued for 20 h. Water (3 ml) and acetic acid (3 ml) were added and the solution was heated at reflux for 4 h. The mixture was poured into 8% sodium bicarbonate solution (60 ml) and extracted with dichloromethane (3×30 ml). The combined, dried organic extracts were evaporated to give a solid (935 mg) which was purified by FCC eluting with System A (200:10:1) to give a solid (310 mg). This material was dissolved in absolute ethanol (5 ml) and treated with a solution of maleic acid (118 mg) in absolute ethanol (2 ml). The solvent was removed in vacuo and the residue was triturated with dry ether (3×10 ml) to give the title compound (413 mg), m.p. 125°–128°.

Water Analysis Found: 1.79% w/w≡0.43 mol $H_2O$.
Analysis Found: C,61.3; H,5.4; N,12.9; $C_{18}H_{18}N_4O.C_4H_4O_4.0.43H_2O$ requires C,61.4; H,5.4; N,13.0%.

EXAMPLE 3

1,2,9,10-Tetrahydro-8-[(5-methyl-1H-imidazol-4-yl)methyl]pyrido[3',4':4,5]pyrrolo[1,2,3-de][1,4]benzoxazin-7(8H)-one maleate 1,2,9,10-tetrahydropyrido[3',4':4,5]pyrrolo[1,2,3-de][1,4]benzoxazin-7(8H)-one (350 mg) and 4-(chloromethyl)-5-methyl-1-(triphenylmethyl)-1H-imidazole (686 mg) were treated according to the method of Example 2 to give the title compound (565 mg) as a solid, m.p. 149°–151°.

Analysis Found: C,60.0; H,5.1; N,12.6; $C_{18}H_{18}N_4O_2.C_4H_4O_4$ requires C,60.3; H,5.1; N,12.9%.

EXAMPLE 4

4,5,7,8,9,10-Hexahydro-10-[(5-methyl-1H-imidazol-4-yl)methyl]-11H-azepino[4,3-b]pyrrolo[3,2,1-hi]indol-11-one maleate 4,5,7,8,9,10-Hexahydro-11H-azepino[4,3-b]pyrrolo[3,2,1-hi]indol-11-one (43 mg) and 4-(chloromethyl)-5-methyl-1-(triphenylmethyl)-1H-imidazole (159 mg) were treated according to the method of Example 2, except that the FCC eluant was System A (100:15:1), to give the title compound (57 mg) as a solid, m.p. 173°–176°.

Analysis Found: C,63.4; H,5.8; N,12.8; $C_{23}H_{24}N_4O_5$ requires C,63.3; H,5.5; N,12.8%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

| Direct Compression Tablet | |
| --- | --- |
| | mg/tablet |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

INJECTION FOR INTRAVENOUS ADMINISTRATION

| | mg/ml | |
| --- | --- | --- |
| Active Ingredient | 0.05 | 1.0 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:
1. A compound of formula (I)

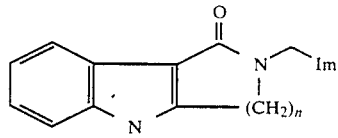

wherein n represents 2 or 3; Im represents an imidazolyl group of the formula:

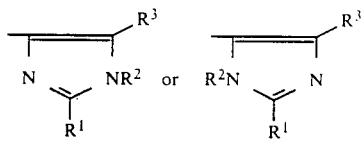

wherein one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same of different, represents a hydrogen atom or a $C_{1-6}$alkyl group; Y represents a group $-(CH_2)_m-$, wherein m represents 2, 3 or 4; or Y represents a group $-X(CH_2)_p-$, wherein p represents 2 or 3, X represents an oxygen or a sulphur atom or a group NR$^4$, where R$^4$ is a C$_{1-6}$alkyl group, and X is attached to the benzene ring moiety of the molecule; or a physiologically acceptable salt or solvate thereof.

2. A compound according to claim 1 in which R$^1$, R$^2$ and R$^3$ each independently represent a hydrogen atom or a C$_{1-4}$alkyl group.

3. A compound according to claim 1 in which R$^1$ and R$^2$ each represent a hydrogen atom, and R$^3$ is a C$_{1-3}$alkyl group.

4. A compound according to claim 1 in which Y represents the group —(CH$_2$)$_2$— or —(CH$_2$)$_3$—.

5. A compound according to claim 1 which is 5,6,9,10-tetrahydro-10-[(5-methyl-1H-imidazol-4-yl)methyl]-4H-pyrido[3',4':4,5]pyrrolo[3,2,1-ij]quinolin-11(8H)-one; 4,5,7,8-tetrahydro-9-[(5-methyl-1H-imidazol-4-yl)methyl]pyrido[4,3-b]pyrrolo[3,2,1-hi]indol-10(9H)-one; 4,5,7,8,9,10-hexahydro-10-[(5-methyl-1H-imidazol-4-yl)methyl]-11H-azepino[4,3-b]pyrrolo[3,2,1-hi]indol-11-one; or a physiologically acceptable salt or solvate thereof.

6. A pharmaceutical composition which comprises an effective amount of a compound of formula (I) as defined in claim 1 or a physiologically acceptable salt or solvate thereof together with at least one physiologically acceptable carrier or excipient.

7. A method of treating a condition mediated through 5-HT$_3$ receptors which comprises administering to a patient an effective amount to relieve said condition of a compound of formula (I) as defined in claim 1 or a physiologically acceptable salt or solvate thereof.

* * * * *

UNITED STATES PATENT AND TRADEMARK OFFICE
CERTIFICATE OF CORRECTION

PATENT NO. : 4,997,831
DATED : March 5, 1991
INVENTOR(S) : David E. BAYS et al It is certified that error appears in the above-identified patent and that said Letters Patent is hereby corrected as shown below:

Column 12, claim 1, please delete structural formula (I) and insert the following structural formula:

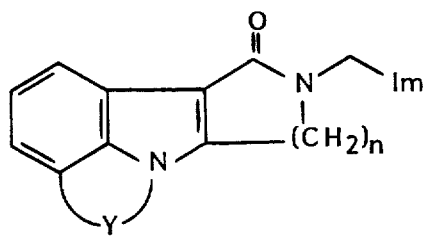

Signed and Sealed this

Twenty-fourth Day of November, 1992

*Attest:*

DOUGLAS B. COMER

*Attesting Officer*      *Acting Commissioner of Patents and Trademarks*